United States Patent [19]

Jonkman et al.

[11] Patent Number: 5,423,769
[45] Date of Patent: Jun. 13, 1995

[54] CARDIOPLEGIA MANAGEMENT SYSTEM

[75] Inventors: Kenneth R. Jonkman; James H. DeVries, both of Grand Rapids, Mich.

[73] Assignee: DLP, Inc., Grand Rapids, Mich.

[21] Appl. No.: 15,212

[22] Filed: Feb. 9, 1993

[51] Int. Cl.$^6$ .............................................. A61M 5/14
[52] U.S. Cl. .................................................. 604/250
[58] Field of Search ............. 604/30, 34, 82, 85, 604/169, 236, 246, 250, 256, 80–85, 86, 174

[56] References Cited

U.S. PATENT DOCUMENTS

| | | | |
|---|---|---|---|
| 2,682,874 | 7/1954 | Hickey | 604/34 |
| 2,954,028 | 9/1960 | Smith | 604/250 |
| 4,425,113 | 1/1984 | Bilstod | 604/34 |
| 4,428,745 | 1/1984 | Williams | 604/250 |
| 4,512,764 | 4/1985 | Wunsch | 604/250 |
| 4,673,161 | 6/1987 | Flynn et al. | 604/34 |
| 4,795,429 | 1/1989 | Feldstein | 604/82 |
| 4,802,650 | 2/1989 | Stricker | 604/34 |
| 5,035,399 | 7/1991 | Rantanen-Lee | 604/250 |
| 5,082,025 | 1/1992 | DeVries et al. | |
| 5,084,031 | 1/1992 | Todd et al. | |
| 5,192,269 | 3/1993 | Poli et al. | 604/82 |
| 5,254,083 | 10/1993 | Gentelia et al. | 604/34 |

OTHER PUBLICATIONS

DLP, Inc.: Product Catalog, Third Edition; 1993; p. 12.

*Primary Examiner*—John D. Yasko
*Assistant Examiner*—Manuel Mendez
*Attorney, Agent, or Firm*—Varnum, Riddering, Schmidt & Howlett

[57] ABSTRACT

A cardioplegia management system comprises an inlet tube adapted for connection to a source of cardioplegic fluid, and at least two supply tubes extending from the inlet tube and in communication therewith, whereby fluid passing through the inlet will be directed to the supply tubes. The system also includes a base, and clamps associated with the supply tubes. Each of the clamps is mounted on the base in a position to selectively clamp and unclamp its respective supply tube, thereby selectively blocking or allowing flow of fluid through the supply tubes.

30 Claims, 3 Drawing Sheets

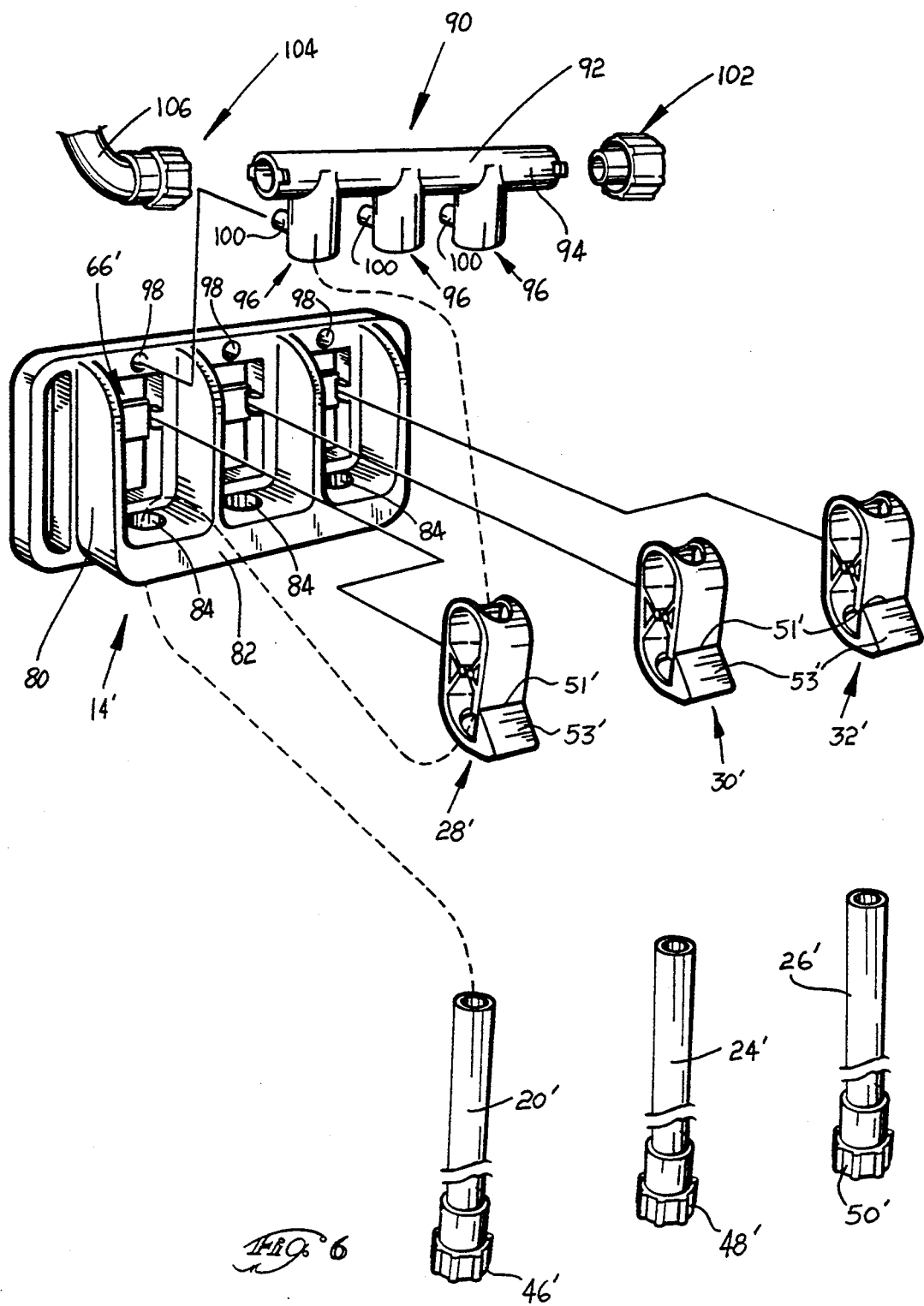

CARDIOPLEGIA MANAGEMENT SYSTEM

BACKGROUND OF THE INVENTION

1. Field of the Invention

This invention relates to a cardioplegia management system for cardioplegia catheters, and more specifically, to such a cardioplegia management system for controlling flow in cardioplegia delivery tubing.

2. Description of Related Art

It has long been recognized in the field of cardiac surgery that when operating on the heart, optimum surgical conditions usually include interruption of its normal functioning. For obvious reasons, an arrested, flaccid heart is preferred during certain cardiac surgical procedures over a beating heart having ordinary blood flowing through it in the normal manner. Thus, it is often the practice to employ extracorporeal cardiopulmonary-bypass techniques in which the heart is isolated from its normal life-sustaining blood supply.

The functioning heart receives its blood supply from the left and right coronary arteries which branch directly from the aorta. About one-half to three-quarters of the heart's blood supply drains through veins flowing into the coronary sinus, which empties directly into the right atrium. A few of the heart's veins, such as the thebesian veins, open directly into the atria or ventricles of the heart.

Cardioplegia, which literally means "heart stop," protects the myocardium, the "heart muscle" as it were, during surgery and, in one technique widely employed, entails infusion of the heart with a cold cardioplegic solution by way of the veins and arteries serving the heart muscle. Typically the heart is chilled and the cold cardioplegic fluid is employed in a manner to maintain the temperature of the heart a few degrees above freezing during the operation to minimize degradation of the heart muscle.

In an alternative technique, the cardioplegic fluid comprises warm blood as a principal constituent.

In any case, cardioplegic fluids typically contain potassium, magnesium, procaine or a hypocalcemic solution, and act to arrest the beating of the heart by depolarizing cell membranes.

The cardioplegic fluid may be administered in an antegrade manner by introducing it into the coronary arteries in the normal direction of blood flow, or in a retrograde manner by introducing it into the cardiac veins in the direction opposite to the direction of normal blood flow, or in alternating retrograde and antegrade administration at the surgeon's direction.

In conventional antegrade cardioplegia, a cannula is employed which terminates in a hollow needle, the needle being inserted through the wall of the aortic root below a clamp which isolates the aorta from the extracorporeal cardiopulmonary-bypass circulatory system. The cardioplegic fluid is introduced through the hollow needle and flows through the coronary arteries in the normal direction of blood flow. Examples of appropriate cannula assemblies for this purpose are described and illustrated in U.S. Pat. No. 4,596,552, issued Jun. 24, 1986 in the name of J. H. DeVries, and U.S. Pat. No. 5,151,087, issued Sep. 29, 1992 in the name of K. R. Jonkman, both assigned to the assignee of the present invention.

Retrograde cardioplegia is conventionally administered by first inserting a balloon catheter within the coronary sinus, inflating the balloon to engage the wall of the coronary sinus and thus form a seal against backflow of fluid from the coronary sinus into the right atrium, and then perfusing the cardioplegic fluid backwards through the coronary blood vessels.

Many surgeons prefer to be able to administer either antegrade or retrograde cardioplegia as and when they choose during the course of the surgery. In such instances, a perfusion set provided with a selection system is employed to connect the antegrade and retrograde catheters to a common source of cardioplegic fluid and to alternate selectively between antegrade and retrograde delivery of the fluid to the heart.

One selection system employs a three-way switch or valve operable to direct the cardioplegia flow into either one or the other of the catheters, or, in an "off" position, to prevent flow in each of the catheters. Such a system is described and illustrated in U.S. Pat. No. 5,082,025, issued Jan. 21, 1992 in the names of J. H. DeVries et al. and assigned to the assignee of the present invention.

Some surgeons prefer instead to use a pair of Roberts-type occluding clamps, one mounted on each of the supply tubes, to select antegrade or retrograde delivery of the cardioplegia flow to the heart or to prevent flow altogether. For quick visual verification of the supply lines, the Roberts clamps may be color-coded, with one color representing antegrade delivery and another color representing retrograde delivery.

SUMMARY OF THE INVENTION

In one aspect of the invention, a cardioplegia distribution set comprises an inlet tube adapted for connection to a source of cardioplegic fluid, and at least two supply tubes extending from the inlet tube and in communication therewith, wherein fluid passing through the inlet will be directed to the supply tubes. The cardioplegia management system also includes a base, and a clamp associated with each of the supply tubes. Each of the clamps is mounted on the base in a position to selectively clamp and unclamp its respective supply tube, thereby selectively blocking or allowing flow of fluid through the supply tubes.

Preferably, the base further comprises at least one hole therethrough whereby the base may more easily be clamped to a stationary structure during an operation.

Each of the clamps preferably comprises a coiled body formed of a flat strip of resilient material and having a first end and a second end. A pair of openings penetrate through the material of the body receive the supply tube. At least one projection extends from the coiled body toward the supply tube. A catch near the second end of the coiled body receives the first end of the body and prevents the body from uncoiling, thereby when the first end of the body end is held by the catch, the projection pinches the supply tube to prevent flow through the supply tube. Preferably, a tab extends outwardly from the clamp body adjacent the catch, and is disposed so that pressure on the tab will tend to pull the catch away from the end of the clamp body, thereby releasing the clamp body end from the catch.

Preferably, the base further comprises a series of wells adapted to receive the clamp bodies. The wells in the base may further comprise at least one catch extending inwardly of the well, and adapted to engage the clamp body.

Preferably, each of the clamps is a different color. A connection luer may be provided on each supply hose, and made the same color as the clamp on the same supply hose.

In another aspect of the invention, a base is provided for a cardioplegia system comprising an inlet tube, a branching connector attached to the inlet tube, at least two supply tubes connected to the branching connector, and an occluding clamp on each supply hose. The base comprises a flat body, and a connecting means on the body for connecting each of the occluding clamps to the body. The connecting means may comprise a well adapted to receive an occluding clamp. The base may further comprise at least one catch extending inwardly of the well and adapted to engage the clamp.

Other features and advantages of the invention will be apparent from the ensuing description in conjunction with the accompanying drawings.

BRIEF DESCRIPTION OF THE DRAWINGS

In the drawings:

FIG. 6 is an exploded perspective view of a second cardioplegia management system according to the invention which includes a clamp base modified from the clamp base of FIGS. 4 and 5.

DETAILED DESCRIPTION OF THE DRAWINGS

Figure 1:
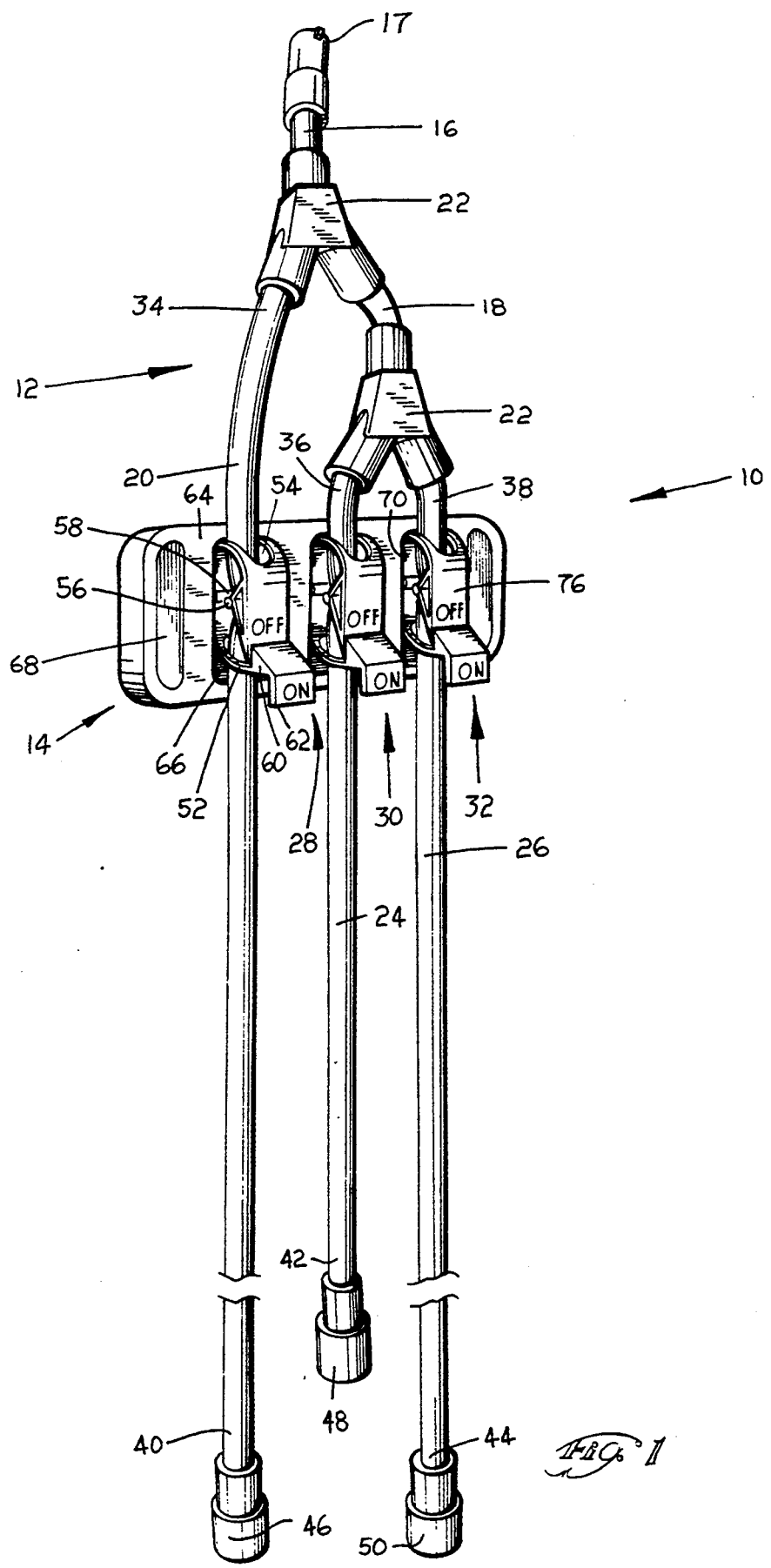
FIG. 1 is a perspective view of a first cardioplegia management system according to the invention.

Referring now to the drawings and to FIG. 1 in particular, a cardioplegia management system 10 comprises a tubing set 12 and a clamp base 14.

The tubing set 12 includes an inlet tube 16 which, by way of a Y-connector 22, branches into a branch tube 18 and a retrograde supply tube 20. The inlet tube 16 is provided with a female luer fitting 17 by which it may be connected to a source of cardioplegic fluid (not shown). The branch tube 18 further branches into an antegrade supply tube 24 and a spare supply tube 26, by way of a second Y-connector 22.

Each of the retrograde, antegrade and spare supply tubes 20, 24, 26 is equipped with a manually actuable Roberts-type occluding clamp 28, 30, 32, respectively, which may be opened or closed to permit or prevent flow of fluid through the associated supply tube. It will be recognized that Roberts occluding clamps, their function, and their manner of operation are well known and therefore need not in themselves be described and illustrated with great particularity.

Each of the supply tubes 20, 24, 26 is connected at its proximal end 34, 36, 38 to the respective Y-connector 22. At the distal end 40, 42, 44 of each of the supply tubes locking male luer fittings 46, 48, 50 are provided for interconnection to cardioplegia delivery catheters (not shown).

Figure 2:
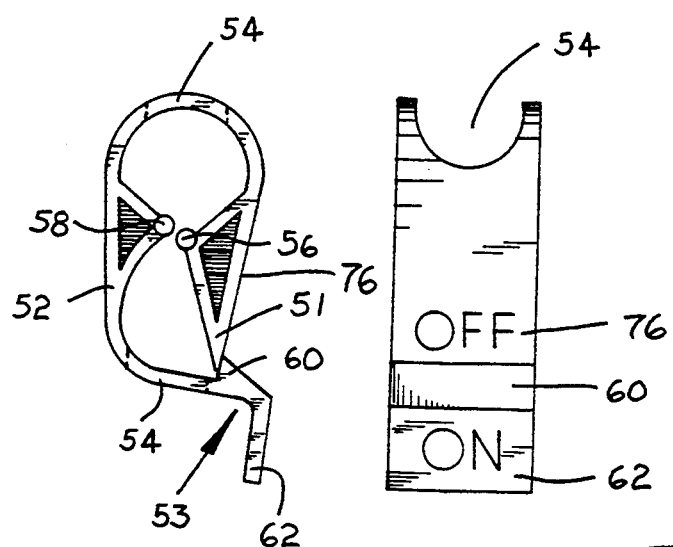
FIG. 2 is a side elevation of a clamp of the cardioplegia management system of FIG. 1.
Figure 3:
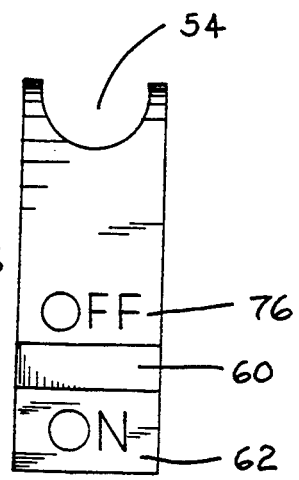
FIG. 3 is a front elevation of the clamp of FIG. 2.

Referring now particularly to FIGS. 2 and 3, each clamp 28, 30, 32 is largely conventional in form and comprises a flexible and resilient body 52 coiled in a generally oval configuration which terminates in a first end 51 and a second end 53 adjacent to and engaged with the first end when the clamp is in the closed condition shown in FIG. 2, as described with greater particularity hereinbelow.

The clamp body 52 is provided with aligned apertures 54 for receiving a section of flexible tubing (not shown in FIGS. 2 and 3), and first and second inwardly facing projections 56, 58. The second end 53 of the body 52 is formed with a detent 60 for engaging the first end 51 of the body 52, in which position the projections 56, 58 are held in close proximity with one another in the manner depicted in FIG. 2, in which position they will act to clamp tightly and thus occlude the aforesaid section of tubing when it is received in the clamp body.

Figure 4:
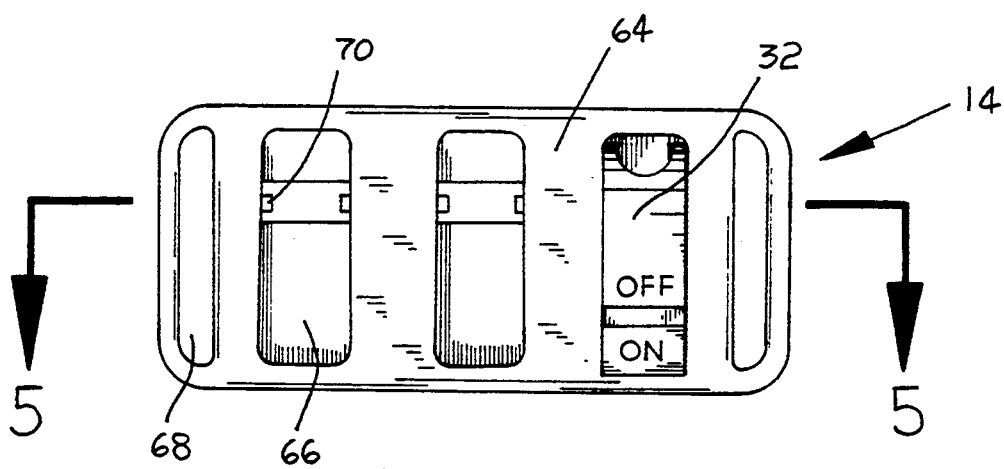
FIG. 4 is a front elevation of the clamp base of the cardioplegia management system of FIG. 1, showing one clamp in place.
Figure 5:
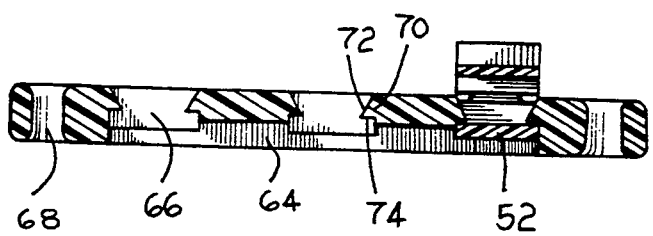
FIG. 5 is a cross-sectional view of the clamp base, taken along section line 5—5 of FIG. 4.

It should be noted that for use in association with the form of the clamp base 14 represented in FIGS. 1, 4 and 5, each clamp 28, 30, 32 is preferably formed with an additional element not found in conventional Roberts clamps and comprising, namely, a release tab 62 located adjacent to the detent 60 at the second end 53 of the clamp body 52. The tab 62, if provided, affords greater convenience in disengaging the detent 60.

In well-known manner, when the clamp is in the open or non-occluding condition (not shown), inward digital pressure applied to the clamp body 52 at a surface 76 thereof near its first end 51 acts to depress the first end and cam it over an inclined surface of the second end 53 until it snaps beneath and is engaged by the detent 60 to hold the body in the closed or occluding condition represented in FIG. 2. Digital pressure applied to the release tab 62 in the same direction will act to disengage the detent 60 from and release the first end 51 of the clamp body, thereby permitting the clamp body to assume its open position in which its ends 51 and 53 are spaced from each other and the projections 56, 58 part further from each other to unclamp or release from occlusion any tubing disposed therebetween.

Referring particularly to FIGS. 4 and 5, the clamp base 14 of FIG. 1 comprises a flat, generally rectangular body 64 formed with three rectangular wells 66, each dimensioned to receive one of the clamp bodies 52. Also formed in the body 64 is an elongated aperture 68 at each end thereof for attaching the clamp base 14 to a drape or towel (not shown) during surgery.

As shown particularly in FIG. 5, a pair of wedge-shaped detents 70 extend into each well 66 from either side thereof to secure the body 52 of a Roberts clamp within the respective well. Each detent is formed by an inclined upper surface 72 and a flat lower surface 74. When a clamp body 52 is pressed into the well, it is readily cammed over the inclined surfaces 72 to pass beneath the detents 70, where it is held in place by the flat lower detent surfaces 74.

In operation, the inlet tube 16 is connected to a source of cardioplegic fluid and the retrograde and antegrade supply tube luer fittings 46 and 48 are connected to suitable retrograde and antegrade cardioplegia catheters (not shown), respectively. The clamp base 14 is secured to a drape or towel covering the patient in conventional manner; e.g., by means of a towel clamp. The spare supply tube 26 is available to be used, for example, in bathing the external surface of the heart with cardioplegic fluid to assist in cooling the heart during surgery.

For convenience, each of the clamps 28, 30, 32, and each of the luer fittings 46, 48 and 50, may be color-coded; e.g., red for antegrade, blue for retrograde, and white for spare. Also, on the surface 76 near its first end 51, the body 52 is preferably marked with the word "OFF", as shown, to indicate that pressing the surface 76 will close the clamp by pinching the tube within between the projections 56, 58. Similarly, the release tab 62 is preferably marked with the word "ON."

Turning now to FIG. 6, a second cardioplegia management system 10' according to the invention is shown, elements corresponding to those of FIGS. 1 to 5 being identified by like reference characters. In this embodiment, to prevent accidental opening or closing of the clamps 28', 30', 32' during a surgical procedure, upstanding guard partitions or ridges 80 may be provided alongside each clamp base well 66' for reasons of safety or security. Specifically, the ridges should extend outwardly of the base 14' to the extent that one must introduce a finger or thumb between adjacent ridges 80 to open or close one of the clamps 28', 30', 32', whereby the possibility of inadvertent opening or closing of one or more clamps is substantially lessened.

A lower ridge 82 may also be provided below the wells 66' for further safety. Preferably, the lower ridge 82 joins the ridges 80 so that they extend from it. Three openings 84, each communicating with a respective one of the wells 66', are provided in the lower ridge 82 to permit the supply tubes 20', 22', and 24' to be passed through the lower ridge.

The clamps 28', 30', 32' omit the clamp tab 62 of clamps 28, 30, and 32. In the embodiment of FIG. 6 the second end 53' of each clamp is simply moved away from the first end 51' to release the latter, and this action may be facilitated by squeezing the second end and the lower ridge 82 together between thumb and forefinger. However, if desired, the clamp base 14' may be enlarged and the wells 66' elongated as desired to provide space for clamps provided with clamp tabs in the manner of the tabs 62 shown in FIGS. 2 and 3.

In the arrangement shown in FIG. 6, the Y-connectors 22 of FIG. 1 have been replaced by a manifold 90. The manifold comprises a main tube 92 provided with a female luer fitting 94 at either end thereof, and three depending branches 96, extending from and normal to the main tube 92. Each branch 96 corresponds to one of the supply tubes 20', 22', 24', and is adapted to receive the corresponding end thereof firmly therewithin to form a fluid tight connection. The manifold 90 is connected to the clamp base 14' by means of three apertures 98 formed in the base 14', one above each of the wells 66', and adapted to receive therewithin three corresponding lugs 100, each extending outwardly from and normal to a respective one of the branches 96.

In assembling the system shown in FIG. 6, a cap 102 in the form of a closed-end male luer fitting is interconnected with one of the female luer fittings 94 to close and seal the respective end of the main manifold tube 92. A male luer fitting 104 provided at one end of a cardioplegia source tube 106 (connected at its opposite end, not shown, to a source of cardioplegic fluid, also not shown) is fitted over the other of the female luer fittings 94. The cap 102 and source tube 106 may be reversed to allow the source tube to communicate with the manifold 90 at the end thereof opposite to that shown, as may be convenient. The capped end of the main manifold tube 92 may also be connected with an additional supply line (not shown), for supplying cardioplegic fluid to additional areas of the heart.

By now it will have been recognized that the modified clamp base 14' of the second embodiment, incorporating the guard ridges 80 and 82, may be employed for greater security in place of the clamp base 14 in the cardioplegia management system 10 of FIG. 1, retaining the Y-connectors 22 for dividing the flow of cardioplegic fluid among the three supply tubes 20, 24 and 26. Such an arrangement provides not only safety but ease and convenience in assembly and relatively inexpensive construction. If the manifold 90 is omitted in this manner, it follows, of course, that the apertures 98 may also be omitted from the clamp base 14'.

Each of the cardioplegia management arrangements disclosed herein according to the invention provides a convenient system to organize and manage the various cardioplegic fluid supply tubes and occluding clamps in a crowded operating environment. The surgeon may visually verify the status of the connections and clamps promptly and with ease. Also, the simplicity of construction promotes reliability.

While the invention has been particularly described in connection with certain specific embodiments thereof, it is to be understood that this is by way of illustration and not of limitation, and the scope of the appended claims should be construed as broadly as the prior art will permit.

What is claimed is:

1. A cardioplegia distribution system comprising a clamp base, and a plurality of manually actuable occluding clamps for selective control of flow in a plurality of cardioplegia supply tubes associated with the clamps, the base comprising a planar panel having a rear bearing surface and a front mounting surface, each clamp having a digitally engageable closure engagement surface, each clamp being mounted to the front mounting surface and oriented so that digital pressure applied to the closure engagement surface toward the panel closes the clamp, whereby when the rear bearing surface abuts an independent support surface, the clamps can be closed with one finger without grasping the base.

2. A cardioplegia management system according to claim 1, wherein the base includes means to facilitate securing the base from movement during surgery.

3. A cardioplegia management system according to claim 2, wherein the base securing means comprises at least one aperture extending through the base.

4. A cardioplegia management system according to claim 2, wherein the base securing means comprises a pair of apertures extending through the base and disposed at opposite ends thereof.

5. A cardioplegia management system according to claim 1, wherein the clamp base includes guard means for preventing inadvertent actuation of clamps mounted by the clamp base.

6. A cardioplegia management system according to claim 1, including a manifold comprising a distribution tube having at least one inlet adapted for connection with an inlet tube and a plurality of outlet branches each adapted to be connected with a supply tube, and means for securing the manifold against movement relative to the clamp base.

7. A cardioplegia distribution system comprising a clamp base, and a plurality of manually actuable occluding clamps mounted on the base for selectively controlling flow in a plurality of cardioplegia supply tubes associated with the clamps, each of the clamps comprising a body formed of resilient material and having:

means for receiving a length of one of the supply tubes;

clamping means carried by the body and disposed to be juxtaposed to said length of one of the supply tubes;

detent means for releasably retaining the body in a clamping condition;

the clamping means being adapted to clampingly engage said length of one of the supply tubes when the body is in said clamping condition; and engagement means for placing the body into said clamping condition in response to digital pressure applied against the engagement means toward the clamp base.

8. A cardioplegia management system according to claim 7, wherein the clamp base includes a plurality of wells formed therein, each of the wells being shaped and dimensioned to receive the body of one of the clamps snugly therein.

9. A cardioplegia management system according to claim 8, wherein the claim base includes means for retaining the body of each of the clamps in a respective one of the wells.

10. A cardioplegia management system according to claim 9, wherein the clamp retaining means comprises at least one detent extending inwardly of the well and adapted to engage the body of a clamp received in the well.

11. A cardioplegia management system according to claim 7, wherein each of the clamps includes a tab extending outwardly from the clamp body adjacent to the detent means in a disposition whereby digital pressure applied thereto tends to urge the detent means in a direction to release the clamp body from the clamping condition.

12. A cardioplegia management system according to claim 7, wherein each of the clamps is a color different from the color of at least one other of the clamps.

13. A cardioplegia management system according to claim 12, wherein the color of each of the clamps is selected to coincide with the color of an element of the supply tube to be received in the clamp.

14. A cardioplegia management system according to claim 7, wherein the clamp base includes guard means comprising at least one ridge extending outwardly from the base adjacent to at least one of the clamps for preventing inadvertent actuation of the clamp.

15. A cardioplegia management system according to claim 7, including a manifold comprising a distribution tube having at least one inlet adapted for connection with an inlet tube and a plurality of outlet branches each adapted to be connected with a supply tube, and means for securing the manifold against movement relative to the clamp base.

16. A cardioplegia management system according to claim 7, wherein the clamp base includes means to facilitate securing the base from movement during surgery.

17. A cardioplegia management system according to claim 16, wherein the base securing means comprises at least one aperture extending through the base.

18. A cardioplegia management system according to claim 16, wherein the base securing means comprises a pair of elongate apertures extending through the base and disposed at opposite ends thereof.

19. A cardioplegia distribution system according to claim 1 wherein each of the clamps further comprises a digitally engageable opening engagement surface oriented so that digital pressure against the opening engagement surface toward the panel opens the clamp.

20. A cardioplegia distribution system according to claim 1 wherein each of the clamps comprises a first occluding member and a second occluding member, the occluding members being disposed on opposite sides of one of said supply tubes, means between the occluding members biasing the occluding members away from each other, and a detent means on one of the occluding members for holding said one occluding member adjacent to the other of said occluding members and the supply tube therebetween for occluding the supply tube disposed between said occluding members.

21. A cardioplegia distribution system according to claim 20 wherein the first occluding member is mounted to the front mounting surface of the base and the closure engagement surface is provided on the second occluding member.

22. A cardioplegia distribution system according to claim 21 further comprising a well in said planar panel opening at the front surface thereof, the well being shaped to receive the first occluding member securely therewithin.

23. A cardioplegia distribution system according to claim 22 wherein the base further comprises a catch extending toward the well and abutting the first occluding member to hold the first occluding member in the well.

24. A cardioplegia distribution system according to claim 21 wherein each of the detent means comprises a pivotable portion of the respective first occluding member and a lip on the pivotable portion abutting the respective second occluding member to hold the occluding members adjacent to each other and the supply tube therebetween, and wherein the first occluding member further comprises a digitally engageable opening engagement surface comprising a tab on the pivotable portion of the first occluding member adjacent to the detent means and oriented to pivot the pivotable portion and the tab away from the second occluding member under a force applied against the tab toward the front mounting surface.

25. A cardioplegia distribution system according to claim 21 further comprising a plurality of guard ridges adjacent to the clamps and extending outwardly from the front mounting surface a distance greater than that by which the clamps extend outwardly from the front mounting surface, whereby the guard ridges protect the clamps against accidental opening and closure.

26. A cardioplegia distribution system according to claim 25 wherein the clamps are arranged in side-by-side relationship and the ridges are oriented between the clamps and laterally adjacent to the clamps.

27. A cardioplegia distribution system comprising a planar clamp base having a rear bearing surface, a front mounting surface, and means for mounting a plurality of manually actuable occluding clamps each having a digitally engageable closure engagement surface for selective control of flow in a respective one of a plurality of cardioplegia supply tubes associated with the clamps, the mounting means orienting the clamps so that digital pressure applied against the closure engagement surface toward the panel acts to close the clamp, whereby with the rear bearing surface abutting an independent support surface, the clamps can be closed with one finger without grasping the base.

28. A cardioplegia distribution system according to claim 27 wherein the mounting means for each clamp comprises a rectangularly shaped well in the base having spaced side walls disposed to frictionally engage a clamp therebetween.

29. A cardioplegia distribution system according to claim 27 wherein the mounting means for each clamp further comprises a catch extending from the base toward the well, the catch being shaped to abut and hold a portion of a clamp received within the well.

30. A cardioplegia distribution system according to claim 28 further comprising a mounting aperture for receiving a portion of a surgical drape to secure the clamp base to the drape.

* * * * *